US008815298B2

(12) United States Patent
Peter Moloney

(10) Patent No.: US 8,815,298 B2
(45) Date of Patent: Aug. 26, 2014

(54) THERAPEUTIC COMPOSITION COMPRISING HONEY OR A HONEY DERIVATIVE

(75) Inventor: Anthony Peter Moloney, Queensland (AU)

(73) Assignee: Medihoney Pty Ltd, Richlands, Queensland (AU)

( * ) Notice: Subject to any disclaimer, the term of this patent is extended or adjusted under 35 U.S.C. 154(b) by 863 days.

(21) Appl. No.: 11/106,473

(22) Filed: Apr. 15, 2005

(65) Prior Publication Data

US 2005/0255166 A1 Nov. 17, 2005

Related U.S. Application Data

(63) Continuation-in-part of application No. 10/639,585, filed on Aug. 13, 2003, now abandoned.

(30) Foreign Application Priority Data

Aug. 13, 2002 (AU) .............................. 2002950744

(51) Int. Cl.
| A61K 35/64 | (2006.01) |
| A61L 15/48 | (2006.01) |
| A61L 15/40 | (2006.01) |
| A61L 15/34 | (2006.01) |

(52) U.S. Cl.
CPC ................. A61L 15/48 (2013.01); A61L 15/40 (2013.01); A61K 35/644 (2013.01); A61L 15/34 (2013.01)
USPC ............................ 424/539; 424/420; 424/445

(58) Field of Classification Search
None
See application file for complete search history.

(56) References Cited

U.S. PATENT DOCUMENTS

| 4,075,320 A * | 2/1978 | Ritter et al. ..................... 424/84 |
| 4,481,326 A * | 11/1984 | Sonenstein .................. 524/377 |
| 4,902,683 A * | 2/1990 | Amin et al. ................... 514/206 |
| 4,990,514 A * | 2/1991 | Bruey ............................. 424/84 |
| 5,980,875 A | 11/1999 | Mousa |
| 6,171,604 B1 | 1/2001 | Mousa |
| 6,280,751 B1 | 8/2001 | Fletcher et al. |
| 6,451,339 B2 * | 9/2002 | Patel et al. .................... 424/451 |
| 6,482,442 B1 * | 11/2002 | Dado ............................. 424/539 |
| 2001/0033848 A1 * | 10/2001 | Jacobson et al. .............. 424/401 |
| 2003/0053961 A1 * | 3/2003 | Eccard ........................... 424/47 |

FOREIGN PATENT DOCUMENTS

| CN | 1088838 | 7/1994 |
| WO | WO 01/67888 A1 | 9/2001 |
| WO | WO 02/00269 A1 | 1/2002 |
| WO | WO 02/30467 A2 | 4/2002 |

OTHER PUBLICATIONS

Kalam et al., Annals of Plastic Surgery, Feb. 2003, vol. 50, No. 2, pp. 143-148.*
Molan, P.C., *Potential of Honey in the Treatment of Wounds and Burns*, Am. J. Clin. Dermatol, 2001, 2(1): 13-19.
Molan, P.C., *Why Honey is Effective as a Medicine: 1. Its use in modern medicine*, Bee World 1999, 80(2): 80-92.
Molan, P.C., *Why Honey is Effective as a Medicine: 2. The scientific explanation of its effects*, Bee World 82(1); 22-40.
Habashy et al., "Anti-inflammatory effects of jojoba liquid wax in experimental models," Pharmacol Res (2005) 51:95-105.
Harry-O'Kuru et al., "Synthesis and characterization of tetrahydroxyjojoba wax and ferulates of jojoba oil," Industrial Crops and Products (2005) 22:125-133.
Molan and Allen, "The effect of gamma-irradiation on the antibacterial activity of honey," J Pharm Pharmacol (1996) 48:1206-1209.
Patel et al., "Chemical and physical analyses of wax ester properties," J Insect Sci (2001) 1.4:1-7.
Postmes et al., "The sterilization of honey with cobalt 60 gamma radiation: a study of honey spiked with spores of *Clostridium botulinum* and *Bacillus subtilis*," Experientia (1995) 51:986-989.

* cited by examiner

*Primary Examiner* — Jon P Weber
*Assistant Examiner* — Teresa E Knight
(74) *Attorney, Agent, or Firm* — Morrison & Foerster LLP

(57) ABSTRACT

A therapeutic composition is described comprising honey or a honey derivative, a surfactant, and at least one topical carrier or vehicle selected from the group consisting of a fatty ester, a wax and a wax-like compound; wherein the composition has been subjected to a sterilization effective dosage of radiation, and wherein the topical carrier or vehicle, when subjected to that dosage, does not substantially modify the properties of the composition present before the sterilization.

19 Claims, No Drawings

THERAPEUTIC COMPOSITION COMPRISING HONEY OR A HONEY DERIVATIVE

This is a Continuation-In-Part of application Ser. No. 10/639,585 filed Aug. 13, 2003 now abandoned.

FIELD OF THE INVENTION

The present invention relates to therapeutic compositions and in particular compositions including honey or honey derivatives.

BACKGROUND OF THE INVENTION

Honey has been used as a natural remedy and therapeutic aid since ancient times. The anti-microbial properties of honey have long formed part of both folk and scientific knowledge. Applications for honey have included topical application for wounds, ulcers, burns and similar conditions. Honey has also been known to be used as a demulcent for use in the gastrointestinal tract for soothing or allaying irritation of inflamed or abraded surfaces. Therapeutic benefits of honey use are manifested by a reduction in inflammation, swelling and pain; prevention and control of infection in a wound; reduction in malodour and exudate; assisted debriding of wounds and improved granulation and epithelialisation of new tissue. These advantages help promote the rapid healing of a wound with minimal scarring.

Whilst these properties encourage the use of honey as a wound healing agent and provide a moist wound environment, regarded as beneficial to the healing of wounds, use has been mainly restricted to unadulterated honey which has been applied in various forms of wound dressings and treatments. Application of honey directly presents difficulties arising from some inherent properties of the material. Due to its relatively low viscosity and fluid nature, plus natural "stickiness", honey tends to contaminate the local environment around a treatment region. The disadvantage of direct honey use is accentuated by the fact that honey at body temperature becomes reasonably fluid and migrates from a treatment site to further increase the chance of transfer to unintended areas. Use of honey can be time consuming, messy and impractical.

In using honey, the presence of wound fluid or exudate also dilutes the therapeutic agent exacerbating the problem of diminished contact time with the wound and diminished therapeutic efficacy. Attempts have also been made to address at least some of these problems by combination with other ingredients. Again the outcome has been variable in success rate. It is also recognised that to make clinical use of honey acceptable, it should be sterile (Postmes T, et. al., *Experientia.* 1995, 51(9-10), 986-9). Many of the antibacterial constituents of honey are sensitive to heat and so traditional pasteurisation techniques are not applicable. It has been demonstrated that the antibacterial activity of honey is not lost upon sterilisation by γ-irradiation (Molan P. C., and Allen K. L., *J. Pharm. Pharmacol.,* 1996, 48, 1206-1209). However, it has been observed that the dosage of γ-irradiation required to effect sterilisation may cause breakdown or undesirable changes in the matrix of honey admixtures known to the art. Accordingly, while the therapeutic properties of honey are recognised and appreciated, there remain problems with the practicality of using honey on wounds.

SUMMARY OF THE INVENTION

In one form, although it need not be the only or indeed the broadest form, the invention resides in a composition comprising: a honey or honey derivative; a surfactant; and at least one topical carrier or vehicle selected from the group consisting of a fatty ester, a wax and wax-like compound; wherein the composition has been subjected to a sterilisation effective dosage of radiation, and wherein the topical carrier or vehicle, when subjected to that dosage, does not substantially modify the properties of the composition present before the sterilisation.

Suitably, the "properties" include but are not limited to rheology, consistency, tactility, and viscosity.

The honey may be a single type of honey or may be a combination of one or more honeys. The one or more honeys may be selected for therapeutic properties which may include anti microbial activities. The honeys may be substantially derived from the flowers of one or more *Leptospermum* species. In one embodiment, a honey derivative may be used. A honey derivative may be a modified form of honey formed by any one of various processes known to a skilled addressee. The honey derivative may include a modified honey where one or more components have been fully or partially removed. The honey or modified honey may have components added to it or treated in a manner to improve its functionality.

As defined herein, the term "fatty ester" refers to monoester of a fatty acid and accordingly excludes oils and fats (triglycerides), which are esters of glycerol (propane-1,2,3-triol).

The term "wax" typically refers to a solid, semi-solid material, and sometimes liquid derived from animal (eg. beeswax and lanolin), plant (eg. palm tree, candelilla, cotton and hemp wax) mineral/fossil/oil (eg. montan wax, rod wax, and microcrystalline wax) or synthetic origin (eg. polyethylene wax, ethylene copolymer wax, carbowax, halogenated hydrocarbon waxes, and synthetic mono esters of fatty acids). It is recognised that jojoba extract is a liquid wax, not an oil (Habashy, R. R., et. al., *Pharmacological Research,* 2005, 51, 95-105). The waxes listed above, do not necessarily form a chemically homogeneous group. A wax may made up of various substances including: hydrocarbons (normal or branched alkanes and alkenes), ketones, diketones, primary and secondary alcohols, aldehydes, sterol esters, fatty acids, terpenes and monoesters of fatty acids, typically with at least one long, or very long carbon chain (from 12 up to about 38 carbon atoms). In addition to mixtures, waxes may also be comprised of a single chemical compound, for example, a substantially pure ester of fatty acid (a fatty ester).

For the purposes of this specification, the term "wax" typically refers to a composition comprising about 50% or more by volume of fatty esters, wherein said compounds and compositions: (a) have the capacity to produce pastes or gels with suitable solvents or when mixed with other waxes or surfactants; (c) low viscosity at just above the melting point (distinction from resins and plastics); and (d) have a low solubility in solvents for fats at room temperature, and (e) are resistant to moisture.

In some embodiments the topical carrier or vehicle comprises an ester of a fatty acid and fatty alcohol (a fatty ester). Mixtures of fatty esters are naturally occurring constituents of many waxes. Substantially pure fatty esters and may be prepared by synthetic means. An example of a substantially pure fatty ester is myristyl myristate which has a melting point of about 37-39° C.

In some embodiments the topical carrier or vehicle comprises beeswax. Beeswax is comprised variously of n-alkanes, ketones, 1°- and 2°-alcohols and alkenols, ketones, aldehydes, alkenals, β-diketones, esters, alkanoic acids, dicarboxylic acids, alpha and omega-hydroxy acids, terpenes, oxygen-heterocycles and various aromatic compounds. Its main components are palmitate, palmitoleate, hydroxypalmitate and oleate esters of long-chain alcohols (C30-32) (about 70 to 80% of the total weight). Ethyl esters are also present, the most abundant species being ethyl palmitate, ethyl tetracosanoate, and ethyl oleate. Aliphatic hydrocarbons (from 10 to 18% of heptacosane and nonacosane and other species from 17 up to 35 carbon atoms), unsaturated hydrocarbons from 21 up to 35 carbon atoms with one or two double bonds, sterols (up to 2% as cholesterol, lanosterol, b-sitosterol), pheromones (geraniol, farnesol) and terpenoids are also found. The melting point of beeswax is typically in the range of 62-65° C.

In some embodiments the topical carrier or vehicle comprises Chinese wax. Chinese wax (insect wax) is generally secreted by insects (*Coccus ceriferus*) and laid on tree branches. Besides an important content in esters (about 83%), this wax includes some free acids, alcohols (up to 1%) and hydrocarbons (2 to 3%). Chemically, the esters are formed of chains with 46 up to 60 carbon atoms, the majority of alcohols and acids having 26 or 28 carbon atoms.

In some embodiments the topical carrier or vehicle comprises shellac wax also known as lac wax, which is produced by a cochineal insect (*Tachardia lacca*) native of India. It contains a majority of fatty esters (70-82%), free fatty alcohols (8-14%), acids (1-4%) and hydrocarbons (1-6%). The esters are formed of chains of 28 up to 34 carbon atoms.

In some embodiments the topical carrier or vehicle comprises a constituent of whale Spermaceti, which is extracted, for example, by cooling (11% of the initial oil) from adipose tissues and is also collected from a big cavity in the head of a cachalot (*Physeter macrocephalus*) known as a sperm whale. This product contained predominantly fatty esters (65-95%). The fatty esters were formed essentially of cetyl palmitate (C32) and cetyl myristate (C30). Its melting point is 42-50° C. Spermaceti, after the recent international regulation concerning whale capture, is no longer produced and sold. It is now replaced by synthetic spermaceti made of pure cetyl palmitate or mixtures based on jojoba.

In some embodiments the topical carrier or vehicle comprises epicuticular wax. In plants, the outer covering consists of a hydroxy fatty acid polymer called cutin. The underground parts and healed wound surfaces of plants are covered with an analogous substance, suberin. These substances are frequently mixed with other lipids and form a complex mixture called epicuticular wax. Cutins contain C16 and C18 families of acids. The former is more abundant in growing parts, the later is present in the cuticle of slower-growing plants. These acids may be saturated, unsaturated, mono- or di-hydroxylated. In the cutin structure, a polyester structure exists where cross-linking depends on the availability of secondary hydroxyl groups. In contrast, the major carbon chains of suberins are ω-hydroxy acids and dicarboxylic acids, all with very long chains (>20 carbon atoms). Among the least polar components of plant surface lipids hydrocarbons with the odd number carbon chains (C15 up to C33) are predominant. Aliphatic alcohols in the C20-C34 range are also widespread in plant surface lipids.

In some embodiments the topical carrier or vehicle comprises carnauba wax, which is secreted by leaves of a Brasilian palm tree (*Copernicia prunifera cerifera*), about 100 g for one tree in a year. It contains mainly fatty esters (80-85%), free alcohols (10-15%), acids (3-6%) and hydrocarbons (1-3%). Carnauba wax also contains esterified fatty dialcohols (diols, about 20%), hydroxylated fatty acids (about 6%) and cinnamic acid (about 10%). This last phenolic acid compound may be hydroxylated or methoxylated. This wax is the hard and high melting point wax (melting point: 78-85° C.). Ouricouri wax, which resembles carnauba wax in its physical properties, was extracted from the ouricouri palm (*Syagrus coronata, Cocos coronata*) by scraping the wax from the leaf surface. Its melting point is 81-84° C.

In some embodiments the topical carrier or vehicle comprises Jojoba liquid wax, which is a polyunsaturated liquid wax very resistant to oxidation (melting point: about 7° C.), and is typically produced by pressing from seeds of the jojoba tree (*Simmondsia chinensis*, Euphorbiacae). The wax is formed quite exclusively of alcohols esterified with long-chain fatty acids (more than 98%) with a typical total of 38 to 44 carbon atoms. The fatty acids are commonly 18:1 (about 10%), 20:1 (about 70%) and 22:1 (15-20%) while the fatty alcohols have predominantly 20 and 22 carbon atoms and one double bond. Derivatised forms of jojba liquid wax are also known to the art. (Harry-O'kuru, R. E., et. al., *Industrial Crops and Products*, received 17 Sep., 2003).

In some embodiments the topical carrier or vehicle comprises Montan wax. This wax is typically derived by solvent extraction of lignite or brown coal (sub-bituminous coal) and is a fossilised plant wax and accordingly has many characteristics of vegetal waxes. Typically, Montan wax is a mixture of long chain (C24-C30) esters (62-68 wt %), long-chain acids (22-26 wt %), and long chain alcohols, ketones, and hydrocarbons (7-15 wt %). Montan wax is hard and is one of the most resistant to oxidation.

In addition to the above-mentioned naturally occurring waxes, synthetic wax can be prepared by the reaction of a fatty acid with an alcohol to form a mono-ester of a fatty acid (a fatty ester as defined above). Typically the alcohol is a fatty alcohol. It is established that increasing the carbon chain length of a fatty ester by a carbon atom, has the effect of raising the melting temperature of the wax by 1-2° C. per carbon atom added. Additionally, it is known that symmetric wax esters (ie., whose alcohol and ester components have different chain lengths) typically have a higher melting point than their unsymmetrical counterparts of the same molecular weight. Further, the presence of an ester linkage in a hydrocarbon chain decreases the melting point by approximately 15° C. relative to hydrocarbons containing the same number of carbon atoms, as does the introduction of a methyl function. Similarly, introduction of a degree of unsaturation to the hydrocarbon chain will typically significantly decrease the melting point, with the introduction of a second degree of saturation further reducing the melting point, but not to the extent that the first degree of saturation. It has also been noted that more internally located double bonds and methyl groups tend to decrease the melting point of wax esters more than those same structural changes near the end of hydrocarbon chains. It has been proposed that these changes to the physical properties of wax esters may result from the disruption of lipid packing due to kinks formed in the hydrocarbon chains (Patel, S., et. al., *Journal of Insect Science*, 2001, 1.4, 7 pp).

Both the fatty acid moiety and the alcohol moiety may be substituted to impart desirable physico-chemical properties to the resulting ester. Mono-esters of fatty acids are described by formula II:

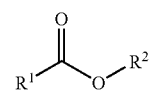

formula II wherein:

$R^1$ is selected from a $C_{7-50}$ optionally substituted alkyl or alkenyl chain; and $R^2$ is selected from an optionally substituted primary or secondary, optionally substituted alkyl or alkenyl chain, with the proviso that the total number of carbon atoms in the molecule is in excess of 11.

As defined herein "optionally substituted" refers to substitution by hydroxyl and/or methyl functional groups.

Also encompassed within the scope of the present invention are wax-like compounds which satisfy the property requirements of wax, whilst not chemically satisfying the compositional requirements of "wax" as defined above.

For example, "wax-like" materials from mineral oils may be derived from petroleum distillates or residues by treatments such as chilling, precipitating with a solvent, or de-oiling. The mineral wax ozocerite typically consists of hydrocarbons (C20-C32) and its melting point is about 90° C.

Another illustrative example of a wax-like compound is candelilla wax which is produced by small shrubs from Mexico, *Euphorbia cerifera* and *E. antisyphilitica* (Euphorbiaceae). The wax is extracted by boiling the plant (to separate the wax and the plant material). The wax floats to the top of the water and is skimmed off and processed. It contains hydrocarbons (about 50% of C29 to C33), esters (28-29%), alcohols, free fatty acids (7-9%), and resins (12-14% triterpenoid esters). Its melting point is 67-79° C. Candelilla has been used mainly mixed with other waxes to harden them without raising the melting point. This wax may be used to improve stability and texture as a substitute to beeswax (melting point: 66-71° C.).

In another example, the wax-like compound is Japan wax, which is a vegetable tallow found in the kernel and outer skin of the berries of *Rhus* and *Toxicodendron* species, including those yielding Japanese lacquer. It contains a high amount of palmitic acid triglycerides (93-97%), long chain dicarboxylic acids including C22 and C23 chains (4-5.5%) and free alcohols (12-1.6%). Its melting point is 45-53° C.

In yet another example, rice bran from the milling of rice, *Oryza sativa*, contains a "wax-like" material mixed with triglycerides which is known as rice bran oil. The melting point of the wax-like component is 75-80° C. The wax contains esters of fatty acids (26 to 30 carbon atoms) and long-chain alcohols (C26 to C30) and a large amount of unsaponifiable matter (55-67%).

It should be noted that the present invention is not dependent on any particular fatty esters, waxes or wax-like compounds and extends to any and all fatty esters, waxes or wax-like compounds with the desired properties irrespective of source. Particularly preferred fatty esters, waxes or wax-like compounds have a melting point in the range of about 37-45° C. and are stable to a sterilisation effective dose of radiation, especially γ-radiation.

As has been described, a wax composition is often composed of a plurality of constituents. It is also the case that a wax composition may be comprised or more volatile and less volatile components at room temperature. Indeed, it is evident that a combination of different waxes, wax-like compounds and fatty esters, each with different chemical properties, could provide a wax composition with sought after physical properties. Further, it is anticipated that it may be desirable to combine a range of waxes, wax-like compounds, and fatty esters with other components such as fatty alcohols, in order to provide "synthetic waxes" with certain desired properties.

For example, fatty esters such as myristyl myristate, cetyl myristate, or cetyl palmitate, and other waxes useful in the present invention may be formulated with each other, or with other chemical compounds such as volatile fatty acid monoesters, fatty alcohols, liquid waxes (jojoba), hydrocarbons and the like, in order to modify the melting point, hardness, color, consistency, tactility, rheology, emollience, viscosity or bonding strength of the wax. By way of further example, fatty esters such as cetyl palmitate or cetyl myristate, which have a melting points in the range of about 43-53° C. and about 54-56° C. respectively, may be formulated with for example, jojoba liquid or lauryl laurate wax which have melting points of about 10° C. and about 24° C. respectively, in order to reduce the melting point of the final wax composition to the preferred range of about 37-45° C. Alternatively a fatty ester, such as cetyl palmitate, may be formulated with ethyl palmitate and myristyl alcohol to provide similarly, a formulation with the desired physico-chemical properties. In another embodiment, ethyl palmitate, which has a melting point of about 24-26° C., may be formulated with jojoba liquid wax and stearyl stearate in order to provide a wax composition with the desired physico-chemical properties. It is anticipated that certain esters, such as for example cetyl palmitate and cetostearyl stearate which are solid at room temperature, may be used to increase the viscosity of emulsions, whereas liquid branched chain esters, such as isopropyl myristate or cetostearyl ethylhexanoate, provide products with good spreading properties.

As noted above, both naturally occurring and synthetic waxes have a range of melting points. For example, beeswax melts at about 62-62° C., cetyl myristate melts at about 54-56° C., cetyl palmitate melts at about 43-53° C., ethyl palmitate (a constituent of beeswax) at about 24-26° C., and Carnauba wax at about 81-84° C. Of additional significance to the melting point, for the practice of the present invention, is the "set-point" of a wax. It is recognised that the melting point of a wax, and the point at which the wax resets, the "set-point" may be different. An intermediary transition phase, upon which the wax begins to become opaque but at which stage it is still mobile, is known as the "cloud point". It is evident that by combining fatty esters, waxes and wax-like compositions, or other compounds with desired properties such as fatty alcohols, that a wax composition with a desirable set-point can thereto be derived, which would be within the skill of a person skilled in the art. In some embodiments, the set-point of a synthetic wax so derived, will be below about 45° C., with the melting point of the wax in excess of about 37° C.

The wax compositions of the present invention may comprise fatty esters such as myristyl myristate, dodecyl hexadecanoate (lauryl palmitate), cetyl palmitate, cetyl myristate, lauryl laurate, stearyl palmitate, stearyl behenate, stearyl stearate, ethyl palmitate, ethyl tetracosanoate, ethyl oleate, cetyl palmitoleate, cetyl laurate, cetyl oleate, jojoba liquid wax, and may further comprise fatty alcohols such as lauryl alcohol, myristyl alcohol, cetyl alcohol, stearyl alcohol, oleyl alcohol, linoleyl alcohol, isostearyl alcohol, palmitoleayl alcohol, with the proviso that the fatty alcohol content does not exceed 50% of the composition by volume.

In other embodiments, the compositions may contain compounds formulated in a manner to have a similar functionality as honey, yet contain little or no honey. In the International Honey Industry, a honey derivative is often applied to a product that is totally or substantially artificial honey and is sold as a honey substitute. These substances are known to a person skilled in the art.

Combinations of honey may include at least one honey with peroxide associated antibacterial activity and at least one other honey with non peroxide associated antibacterial activity. The honey or honeys may be selected on the basis of natural sugar levels to regulate natural crystal formation. The honeys may also be selected on the levels of physiologically active compounds including but not limited to flavonoids, alkaloids, growth regulators and compounds that cause stimulation of TNF-alpha release.

In certain embodiments, the honey or honeys constitute about 50% of the composition. Preferably the honey is present in the range of about 70-90% of the composition and most preferably is present in a concentration at or around about 80% of the composition. The percentage compositions in this specification are calculated on percentage weight/weight (% wt/wt).

Suitably, the wax or wax like material has a set-point of about 45° C. or less. Preferably, fatty ester, wax or wax-like compound has a narrow set-point range about 40° C. In some embodiments the wax may be a fatty ester or fatty alcohol. In specific embodiments, the wax is myristyl myristate, an illustrative example of which is Crodamol MM.

The fatty ester, wax or wax-like compound may be present in the range of 1-50% of the composition. Suitably, the fatty ester or wax or wax-like compound is present in the range of 10-30%. In a preferred embodiment the fatty ester, wax or wax-like compound is present at or about 15% of the ointment.

The surfactant may be a low irritant, mild non ionic surfactant. The surfactant may be ethoxylated oil, such as preferably ethoxylated sweet almond oil. The surfactant may alternatively comprise or include ethoxylated caster oil or ethoxylated evening primrose oil. The surfactant may be Crovol A70. The surfactant may be present in the range of 2-10%. Preferably the surfactant is present in the range of 2-7%. Most preferably the surfactant is present at or around 5% of the composition.

By "about" is meant quantity, level, value or amount that varies by as much as 30%, preferably as much as 20%, more preferably as much as 10% and even more preferably by as much as 9%, 8%, 7%, 6%, 5%, 4%, 3%, 2% or 1% to a reference quantity, level value, or amount.

The articles "a" and "an" are used herein to refer to one or to more than one (i.e. to at least one) of the grammatical object of the article. By way of example, "a compound" means one compound or more than one compound.

In a further aspect the invention resides in a method of producing a therapeutic honey ointment, the method comprising the steps of:

heating honey to a temperature which is below a temperature that will cause degradation, complete or partial, of one or more functional enzymes in honey;

combining the at least one topical carrier or vehicle and a surfactant by heating and mixing;

cooling the mixture of at least one topical carrier or vehicle and surfactant until the mixture has a temperature similar to the temperature of the honey; and combining the honey with the carrier or vehicle and surfactant.

The "at least one topical carrier or vehicle" in this context includes fatty esters, waxes and wax-like compounds.

The one or more functional enzymes in honey may be glucose oxidase. The maximum temperature of the heated honey may be about 45° C.

The carrier or vehicle and surfactant mixture may be heated to a temperature range in which the wax is in a liquid phase.

The carrier or vehicle and surfactant mixture may be mixed through the honey with high shear mixing until homogeneous, preferably avoiding overheating of the mixture.

The method may include the step of sterilising the ointment. The ointment can be sterilised by applying one or more doses of gamma irradiation. The gamma irradiation may be provided at levels between 25-35 kGy.

The expression "ointment" in this specification may be understood to extend to any suitable physical state including, but not restricted to a gel, a paste, a cream, a lotion, a balm and a salve.

The method may further include the step of impregnating a bandage or dressing with the ointment for use on a subject.

The method may further include the step of packaging the ointment for distribution.

In a further aspect the invention extends to a method of treating a subject by applying one or more doses of an ointment made according to the above method or comprising the above described ingredients.

DETAILED DESCRIPTION OF THE INVENTION

The present invention is directed to an easy to use, effective and stable honey based composition preferably presented as an ointment. The ointment may be formed from a combination of honey or honey derivative, a surfactant and a wax or wax-like component or fatty ester.

The honey component of the ointment may include a combination of one or more honeys selected for their therapeutic properties. The honeys may be derived from the Australian or New Zealand *Leptospermum* species. The honeys may include a combination of two or more honeys selected for differing but preferably complementary physiological/therapeutic action including those with peroxide and non peroxide antibacterial activity. This combination may ensure a broad spectrum of antibacterial activity. There are many known types of honey. Illustrative examples are described in publications such as *Honey and Pollen Flora*, Clemson A, INKATA PRESS Pty Ltd, Melbourne, 1985 and similar reference works. Honeys may be selected on the basis of the presence of flavonoids which may act as an anti-oxidant resulting in inflammation reduction. Honeys may also be selected for the presence of growth factors which can assist with granulation, epithelialisation and the growth of new tissue to ensure a progressive and satisfactory healing process. The honeys may also be selected on the presence or levels of physiologically active compounds including but not limited to flavonoids, alkaloids, growth regulators and compounds that cause stimulation of TNF-alpha release.

The surfactant is preferably a low irritant, mild chemical. Preferably the surfactant is non ionic as, in general, this class of compounds is milder than ionic surfactants. A preferred surfactant is an ethoxylated triglyceride and in particular sweet almond oil or a derivative thereof. Alternatively it is possible to substitute ethoxylated castor oil or ethoxylated evening primrose oil, preferably in non ionic form.

An example of a commercially available product is CROVOL A70 which is derived from sweet almond oil in an ethoxylated form. The international nomenclature for cosmetic ingredients has allotted the name of PEG-60 almond glycerides to CROVOL A70. This product is a long chain ethoxylate and has been shown to have a very low tendency to irritation. CROVOL A70 has a chemical description as ethoxylated (70% by weight) sweet almond oil (CAS 124046-50-0) and may be obtained from Croda Australia, Villawood, Sydney.

An additional ingredient is at least one topical vehicle or carrier selected from the group consisting of a fatty ester, wax or wax-like compound. Preferably the fatty ester or wax has a melting point above about 37° C. and a set-point below about 45° C. The preferred melting point is selected so that the ointment is substantially non-running at the body temperature of a patient which is usually around 37° C. in a person but may be higher in domestic animals. In general however, the invention is suitable for both veterinary and human use. One means of assessing whether the ointment is non-running is to place a sample on a slope, preferably at 45°, and demonstrate that the sample does not freely flow down the incline at 25° C.

A preferred wax is Myristyl Myristate (CAS 3234-85-3). This is a wax with a low melting point, usually in the range of about 37-43° C. It has good skin softening and lubricating properties. Alternative ingredients may include any mixture of fatty esters, fatty alcohols and other hydrocarbons, that satisfies the condition of having a melting point above about 37° C. and a set-point below about 45° C. This temperature is above normal body temperature but it is also below the denaturing temperature of functional enzymes in honey which is generally accepted to be around 45° C. Most fatty esters have long hydro-carbon chains that are very stable. The ester group of the molecule also provides a stable and non-reactive aspect to the compound, making it safe to use for this application.

An example of a commercially available source of Myristyl Myristate is Crodamol MM which is available from Croda Australia, Villawood, Sydney.

In a preferred method of manufacture, honey is heated to a temperature that will not degrade the functional enzymes, such as glucose oxidase, which occur in honey. Preferably this temperature is about 45° C. Separately, the wax and surfactant are heated while being mixed until both are fully melted. The wax/surfactant mixture is allowed to cool to the temperature of the honey at which time it is added to the honey with high shear mixing until homogenous. The mixing period may be relatively brief. It is preferred to avoid heating honey above the upper identified temperature as such a process may lead to degradation of functional enzymes with resulting diminution of therapeutic effect.

The mixed ointment may then be allowed to cool and be packaged for distribution.

Preferably the ointment is also sterilised particularly to remove or reduce *Clostridium* sp spores and to provide an associated reduction in bioburden levels. The preferred method of sterilisation is through the use of gamma irradiation, preferably at levels between 25-35 kGy. One of the benefits of the present ointment is that it remains substantially stable and homogenous after irradiation at these levels. The current formulation may be described as a fine wax dispersion in a honey matrix. Without wishing to be tied to any one theory, it appears the surfactant acts to keep the wax particles small and enables them to be suspended and dispersed throughout the honey. It has been found that some emulsifiers including lanolin are prone to denaturing or breakdown under irradiation making them unsuitable for use in the present composition.

In one embodiment, the ointment is formulated according to the following proportions:

| Ingredient | Range (% wt/wt) |
| --- | --- |
| Honey or honey derivative | 50-97% |
| Myristyl Myristate | 1-50% |
| Ethoxylated sweet almond oil | 2-15% |

Preferably honey is present in the range of about 75-84%. Myristyl Myristate may be the range of about 15-20% and ethoxylated sweet almond oil may be present in the range of about 1-7%.

In certain embodiments, the composition comprises about 80% honey, about 15% Myristyl Myristate and about 5% ethoxylated sweet almond oil.

It is envisaged that the present ointment may also be used for cosmetic rather than therapeutic purposes. In this case, selection of honeys with therapeutic characteristics is not essential. Honeys may be selected for cosmetic benefits such as providing a general moisturising action. Clearly, honeys may also be selected for the treatment of essentially aesthetic problems such as comedones or pimples. Selected honeys in these cases may be bacteriostatic.

Once produced, the ointment may be packaged and distributed in any suitable fashion. It may be dispensed into tubes. Alternatively it may be formed as part of a wound dressing by impregnation into a wound dressing material. The ointment may be packed into individual screw top containers or it may be delivered in sealed capsules or sachets for single use dispensing and treatment.

The ointment of the present invention may be applied in a wide range of situations and as already noted may be used in both human and veterinary medicine, as well as for human cosmetics. In its simplest form, the ointment may be applied topically to a lesion. The frequency of application may be varied to reflect the severity of the condition and the efficacy of the treatment. It is envisaged that an application rate of up to two to three times daily may be of benefit in some circumstances while application every 2-14 days may be suitable in other circumstances where the contact time is prolonged. The ointment is preferably of suitable viscosity that it may be dispensed or molded or pressed into shape using finger pressure to adopt a configuration suitable for a lesion. That shape may be retained while the ointment is fixed in position by a support bandage or similar.

The ointment may be beneficially utilised in post surgical wounds, sinus wounds, fistulae, burns, donor sites, infected wounds, pressure ulcers, venous ulcers, diabetic ulcers, trauma injuries, catheter exit sites, dental extraction sockets, fungating/malignant wounds, lesions, ophthalmology and surgical procedures. This list is not comprehensive. Viscosity may be selected so that the ointment is suitable for filling wound cavities. Some advantages of the composition will be demonstrated in the following non-limiting Examples.

EXAMPLE 1

Honey ointment according to the present invention was used to treat burns in paediatric patients. The ointment demonstrated an ability to deslough the wound, reduce the bacterial load and assist healing. One child had a deep partial thickness burn to the scalp that had become infected and a hard crusty eschar had formed over the wound. The honey ointment desloughed the wound, cleared the infection and the wound healed without the need for surgical debridement within five days. Another case involved a deep partial thickness burn on a child, that had become infected with bacteria that were resistant to other topical antibacterial products and oral antibiotics. After application of the honey ointment to the burn, the bacterial load was reduced within five days, allowing for successful skin grafting. The honey ointment was easy to apply to gauze dressings, which were then applied to the wounds. The honey ointment washed off easily in a shower. Dressings were changed daily over the period of treatment.

EXAMPLE 2

The honey ointment was tested in a microbiological laboratory against various bacterial organisms, including

*Pseudomonas* sp isolated from wounds and resistant to antibiotics and other antibacterial products including silver sulfadiazine and povidone-iodine. The honey ointment proved very effective against all tested organisms.

EXAMPLE 3

Malodour associated with fungating tumours was reduced with the use of the honey ointment. The honey ointment was applied directly to a melolin dressing which was then applied to a fungating tumour external to the mouth cavity, which had become malodorous. Malodour was reduced within two days. The honey ointment was easy to apply and stayed in place on the wound.

EXAMPLE 4

Leg ulcers and skin tears are well suited to application of the honey ointment. One male patient with poor circulation and a difficult-to-heal leg ulcer infected with *Pseudomonas* sp and *Staphylococcus* sp was treated with honey ointment of the present invention. He had previously been on antibiotics, but as these had not helped clear the infection, he was taken off his oral antibiotics and the honey ointment was used. The honey ointment was applied directly to the wound then covered with either plain gauze or paraffin-impregnated gauze. The dressings were changed daily initially then when the wound was clean, dressings were changed every second day. The honey ointment cleared the infection and the wound was rendered clean and healing. Another male patient had a skin tear that was progressing towards an ulcerous condition and was treated with the honey ointment as described above. The wound healed within two weeks. Other ulcers and skin tears have also been treated successfully with the honey ointment.

EXAMPLE 5

A sacral area ulcer and an infected stump wound resulting from surgery were healed with the use of the honey ointment applied to a dry dressing (Combine™).

EXAMPLE 6

The honey ointment was applied directly to a partial amputation of the foot using a sterile tongue depressor and covered with a dry dressing (Combine™). The wound had been treated with pure honey but the patient had been complaining of leakage from the dressing. The treatment was changed to daily honey ointment dressings and the patient had no further complaints. Healing of the wound was subsequently uneventful.

A small and deep arterial leg ulcer infected with Methicillin-resistant *Staphylococcus aureus* (MRSA) was healed with the use of the honey ointment. Daily dressings of the honey ointment applied to a dry dressing (Combine™) helped clear the infection and heal the wound.

As a result of prior-wound management, a sacral wound on a patient had macerated edges and no granulation at the base of wound. A zinc-based cream was applied around the edges of the wound and the honey ointment was applied to the wound and covered with dry dressings (Combine™) and paraffin-based dressing (Adaptic™) and followed by a film dressing (Opsite™). Dressings were changed daily. Improved granulation of the wound bed was observed, the wound edges improved and the wound size decreased until the patient was sent to another clinical site.

EXAMPLE 7

The honey ointment has also been used to help reduce caesarean section scars. The honey ointment was applied directly to the week-old scar with no dressings required.

EXAMPLE 8

Diabetic wounds have also healed with the use of the honey ointment. The honey ointment was found to be easier to apply to these wounds than pure honey and the healing response was the same as or better than pure honey dressings.

The present ointment may be applied to mucous membranes and may be dispensed into bodily cavities for the treatment of mucous membranes. The ointment may be ingested for beneficial results in some circumstances. The composition of the ointment may be such that at body temperature, compared to room or storage temperature, it will soften and conform to a wound and surface to which it is applied and will remain in place for temperatures up to 37° and preferably up to 40°.

The present invention provides real benefits in the therapeutic use of honey. The use of 100% honey is, as noted above, somewhat problematic. Additionally the use of honey in known methods can be quite irritating particularly to sensitive wounds. The present invention incorporates ingredients which may be of natural origin and which do not have marked side effects such as may arise with mineral based products. The viscosity of the invention is such that it can be easily applied to a wide range of wounds some of which are painful to touch. As the surfactant can be a water soluble, vegetable derived emollient, the ointment can be easily washed off the body and can be irrigated out of body cavities. This advantage is of considerable significance as it provides easy clean-up of both patient and surrounding environments.

Manufacture of the ointment as described provides a product which can slowly dissolve over time in body fluid rather than be subject to immediate dilution and displacement by wound exudate. Additionally the ointment may be suitable for internal use and for effective gamma irradiation sterilisation. The nature of the product makes it practical for bulk manufacture and relatively easy dispensing into packages and containers.

The ingredients of the combination are known to be stable, inert, non irritating and safe to use in therapeutic applications. Further the composition is such that a stable and homogenous mix of ingredients is achieved within the manufacturing temperature restrictions. The present invention reduces the problems associated with raw honey used in the treatment of wounds which may cause stinging and sometimes painful sensations when applied to the wounds of patients. The ointment may be used for cosmetic purposes.

The honey ointment is preferably formulated with natural waxes and oils to provide a high viscosity gel that is easy to apply with good wash off characteristics when dressings are changed.

The honey ointment can be applied either directly to the wound or to the dressing. A thin absorbent dressing with a non/low adhering surface can be used to cover the honey ointment with additional absorbent secondary dressings applied as required.

The frequency of dressing changes required will depend on how rapidly the honey ointment is being diluted by exudate. Daily dressing changes are usual during the initial stages of wound healing. More frequent changes may be needed if the honey ointment is being diluted by a heavily exudating wound. When exudation is reduced, dressing changes can be less regular (2 to 3 days).

The honey present in the honey ointment will be gradually diluted by exudate and absorbed by the dressing. Waxes contained in the honey ointment will remain leaving a protective layer. These waxes can be washed away at each dressing change by rinsing with normal saline or similar products.

The honey ointment provides natural debridement of the wound through autolysis so the wound may appear deeper after the initial dressing changes. The debriding action may also be due to the strong osmotic potential of the honey.

It is within the scope of the invention to add other ingredients known to a skilled addressee for various additional characteristics.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the disclosure.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

What is claimed is:

1. A homogenous composition for treating a patient wherein the composition comprises: at least 50% honey or a honey derivative; 2-15% of ethoxylated sweet almond oil; and 1 to 50% of at least one topical carrier or vehicle which is a fatty ester having a set point of 45° C. or less, wherein the oil constituents of said composition consist of ethoxylated sweet almond oil, and wherein said composition has been subjected to a sterilization effective dosage of radiation.

2. The composition of claim 1 wherein the at least one topical carrier or vehicle comprises myristyl myristate.

3. The composition of claim 1 wherein the composition further comprises or more additional topical carriers or vehicles selected from the group consisting of: fatty ester, synthetic wax, beeswax, vegetal wax, Chinese wax, shellac wax, a spermaceti wax derivative, carnauba wax, and jojoba liquid wax.

4. The composition of claim 1, wherein at least one topical carrier or vehicle has a melting point of about 37° C. or greater.

5. The composition of claim 1 comprising a honey substantially derived from a single floral species.

6. The composition of claim 1 comprising two or more honeys derived from different floral species.

7. The composition of claim 6 wherein at least one honey has peroxide associated activity and at least one other honey has non-peroxide associated activity.

8. The composition of claim 1 wherein the honey or honey derivative constitutes from about 70 to about 90% of the composition.

9. The composition of claim 1 wherein the honey or honey derivative constitutes about 80% of the composition.

10. The composition of claim 1, wherein ethoxylated sweet almond oil constitutes from about 2% to about 10% of the composition.

11. The composition of claim 1, wherein ethoxylated sweet almond oil constitutes about 2% to about 7% of the composition.

12. The composition of claim 1 wherein ethoxylated sweet almond oil constitutes about 5% of the composition.

13. The composition of claim 1 wherein the at least one topical carrier or vehicle constitutes from about 10 to about 30% of the composition.

14. The composition of claim 1 wherein the topical carrier or vehicle constitutes about 15% of the composition.

15. The composition of claim 1, wherein said at least one topical carrier or vehicle consists of myristyl myristate.

16. The composition of claim 1, wherein said composition comprises 80% honey, 15% myristyl myristate and 5% ethoxylated sweet almond oil.

17. A wound dressing comprising a material dressing and the composition of claim 1.

18. A homogenous composition for treatment of a patient, said homogenous composition comprising 80% honey, 15% myristyl myristate and 5% ethoxylated sweet almond oil.

19. A method of treating a subject, human or animal, comprising applying the composition of claim 1 in a therapeutically effective dose to the human or animal subject.

* * * * *